United States Patent

Habermann et al.

[11] Patent Number: 5,217,900
[45] Date of Patent: * Jun. 8, 1993

[54] BIOLOGICAL REACTOR

[75] Inventors: Wolfgang Habermann, Mainz; Ernst-Heinrich Pommer, Limburgerhof; Peter Hammes, Ruppertsberg, all of Fed. Rep. of Germany

[73] Assignee: BASF Aktiengesellschaft, Ludwigshafen, Fed. Rep. of Germany

[*] Notice: The portion of the term of this patent subsequent to Jun. 2, 2004 has been disclaimed.

[21] Appl. No.: 380,730

[22] Filed: Jul. 13, 1989

Related U.S. Application Data

[63] Continuation of Ser. No. 764,328, Aug. 12, 1985, abandoned.

Foreign Application Priority Data

Aug. 18, 1984 [DE] Fed. Rep. of Germany ....... 3430488

[51] Int. Cl.⁵ .............................................. C12M 1/40
[52] U.S. Cl. ................................... 435/288; 435/287; 435/817; 204/403
[58] Field of Search ............... 435/288, 817, 173, 287, 435/299; 204/131, 403, 421, 351, 37.6, 383, 149, 277, 294, 302

[56] References Cited

U.S. PATENT DOCUMENTS

| | | | |
|---|---|---|---|
| 3,764,269 | 10/1973 | Oldham et al. | 204/421 X |
| 4,321,123 | 3/1982 | Nakamura et al. | 204/403 |
| 4,490,464 | 12/1984 | Gorton et al. | 204/403 X |
| 4,514,277 | 4/1985 | Sakurai et al. | 204/421 X |
| 4,670,360 | 6/1987 | Habermann et al. | 204/294 |

Primary Examiner—Robert J. Warden
Assistant Examiner—William H. Beisner
Attorney, Agent, or Firm—Keil & Weinkauf

[57] ABSTRACT

A biological reactor which is operated using microorganisms and/or enzymes and used for the oxidative conversion of organic compounds, and in which the organic compounds to be converted are employed in the presence of a biocatalyst in the reactor space (4) (anode space) and the enzymes are regenerated at a polarized electrode (1), the polarization of the electrode (1) being effected by means of a catalyst electrode (2) which is separated from the reactor space (4) by a polyelectrolyte (3) and is located in an electrolyte space (5), wherein the electrode (1) is prepared from an electrically conductive carbon material which has been partially oxidized on the surface at a potential $\epsilon_h$ of from +1.3 to +10 V in an aqueous oxygen-containing mineral acid.

13 Claims, 6 Drawing Sheets

BIOLOGICAL REACTOR

This application is a continuation of application Ser. No. 764,328, filed on Aug. 12, 1985, now abandoned.

BACKGROUND OF THE INVENTION

The present invention relates to a biological reactor which is operated using microorganisms and/or enzymes and used for the oxidative conversion of organic compounds and in which the organic compounds to be converted are employed in the presence of a biocatalyst in the reactor space and the enzymes are regenerated at a polarized electrode, polarization of the electrode being effected by means of a catalyst electrode which is located in an electrolyte space and separated from the reactor space by a polyelectrolyte.

In industrial microbial processes, which take place under aerobic conditions, the reactors used are operated with oxygen or air for the regeneration of the enzymes or respiration of the microorganisms. In order to ensure that an adequate amount of oxygen is introduced, jet nozzle systems, immersed jet systems and stirrer systems have to be employed. New phase boundaries have to be created constantly by means of thorough mixing in order to ensure good mass transfer, since only the dissolved oxygen takes part in the reaction. This method of introducing oxygen gives rise to high shear forces which damage some or all of the microorganisms and of the enzyme system. Another problem is the control of foam during gassing. To this end, it is often necessary to use expensive non-metabolizable antifoams, some of which remain in the desired product. Hence, mechanical foam inhibitors have been used, but these too caused damage to the microorganisms. Another problem is the sterility of the air introduced; in the case of sensitive products or microorganisms, this air must be free from extraneous organisms.

SUMMARY OF THE INVENTION

It is an object of the present invention to provide a biological reactor which permits the biocatalysts to be regenerated in a simple, more effective manner without damaging them, and to provide techniques for improving the separation of the oxidizing agents, the organic compounds to be converted, and the biocatalysts.

We have found that this object is achieved, in accordance with the invention, if, for controlling the biochemical process, the oxygen in the reactor space is replaced with an anodically polarized electrode which consists of an electrically conductive carbon material which has been subjected to surface oxidation at a potential $\epsilon_h$ of from $+1.3$ to $+10$ V in an aqueous oxygen-containing mineral acid.

The biological reactor comprises means defining a reactor chamber and an electrolyte chamber, said means including a polyelectrolyte which separates the reactor chamber from the electrolyte chamber; an anodically polarized electrode made of an electrically conductive carbon material which has been subjected to a surface oxidation at a potential of $\epsilon_h$ of from $+1.3$ to $+10.0$ V in an aqueous oxygen-containing mineral acid and having immobilized thereon a biocatalyst, said anodically polarized electrode being present in the reactor chamber and separated from the electrolyte chamber by the polyelectrolyte; and a polarizable catalyst electrode which is permeable to ions and electrically conductive, said catalyst electrode being present in the electrolyte chamber and separated from the reactor chamber by the polyelectrolyte.

BRIEF DESCRIPTION OF THE DRAWING

The invention is illustrated with reference to the drawings below.

DESCRIPTION OF THE PREFERRED EMBODIMENTS

An anodically polarized electrode 1 is fixed on a polyelectrolyte 3 (ion exchanger) which separates a reactor space 4 from an electrolyte space 5, and a second polarizable catalyst electrode 2 which is permeable to ions and electrically conductive or connected to the anodically polarized electrode 1 in the reactor space 4 via an external voltage source 6 is located on or near the surface of the polyelectrolyte 3.

The anodically polarized carbon material of the electrode 1 consists of, for example, graphite, graphite wool, anthracite or active carbon which has preferably been partially oxidized electrochemically in an aqueous oxygen-containing mineral acid, eg. nitric acid, phosphoric acid, sulfuric acid or perchloric acid, at a potential $\epsilon_h \geq +1.3$ V, the potential $\epsilon_h$ not exceeding $+10$ V, and then activated by cathodic reduction in a mineral acid. Preferably, the procedure is carried out in aqueous nitric acid at an oxidation potential $\epsilon_h$ of from $+1.8$ to $+2.5$ volt.

To effect anodic oxidation, from 2 to 80, preferably from 30 to 65, % strength by weight aqueous nitric acid is used. The oxidation is carried out at $< +100°$ C., preferably from $+10°$ to $+40°$ C., and at a current density of from 0.1 to 10, preferably from 0.5 to 4, $kA/m^2$ of electrode surface.

Instead of a nitric acid, it is also possible to use aqueous sulfuric acid, phosphoric acid or perchloric acid. When the anodic oxidation is complete, the electrode material is freed from residual oxidizing agent by cathodic reduction in aqueous sulfuric acid, preferably from 5 to 20% strength by weight aqueous sulfuric acid.

Although the method is substantially less effective, oxidation of the graphite surface may also be effected chemically using a nitrogen oxide, preferably nitrogen dioxide, at from $+300°$ to $+800°$ C., or in a chromate-containing mineral acid, e.g. chromate-containing sulfuric acid, phosphoric acid or perchloric acid.

The polarization of the catalyst electrode 2 in the electrolyte space 5 is carried out using an oxidizing agent, e.g. oxygen, hydrogen peroxide, a per compound, chlorine, nitric acid, an iron(III) salt, a cerium(III) salt, a chromium(VI) salt, an acidic vanadate or nitrous gases, which can be used in the electrolyte space 5 in high concentration. The reaction of the oxidizing agents takes place at the surface of the catalyst electrode 2, which is fixed in the electrolyte space 5 and provides good electronic exchange conditions, while the regeneration of the enzyme system and/or microorganisms is effected by electron exchange with the anodically polarized electrode 1 present in the reactor space 4.

When the catalyst electrode 2 is polarized via an auxiliary electrode 7, the overvoltage of the catalyst electrode material in the electrolyte space 5 and the current density are also critical.

Homogeneous and heterogeneous cation or anion exchange membranes are used as polyelectrolytes 3 which constitute the carrier of the catalyst electrode material and the separator between reactor space 4 and oxidation space 5. Ion exchange membranes based on polymers or copolymers of styrene, styrene and divinylbenzene, vinyl chloride and acrylonitrile, olefins, and perfluorinated olefins which possess, as charge-carrying groups, quaternary ammonium, sulfo or carboxyl groups are preferred. Highly crosslinked ion exchange materials which exhibit low swellability, have a high concentration of charge-carrying groups and are scarcely permeable to coions are particularly preferred.

The polarized electrode 1 and the catalyst electrode 2 are in the form of, for example, nets, expanded metal lattices, sintered elements, perforated plates, grids, sponges and the like, the free surface area being about 15-85%, preferably 25-65%, of the electrode surface so that there is an adequate flow of ions. In this embodiment, at least the polarized electrode 1 is coated on the surface with a partially oxidized, electrically conductive carbon material.

To improve the conductivity, it is advantageous if the pores, channels and perforations are partially or completely filled with ion exchange material. To do this, for example, fine-particled ion exchangers can be incorporated with a binder or polystyrene having a molecular weight of 50,000, by introducing, for example, quaternary ammonium groups by chloromethylation and treatment with amines, or introducing sulfo groups by sulfonation. In the case of a composition of this type, the conductivity of the medium in the reactor space is no longer of importance.

Titanium, zirconium, vanadium, tantalum, niobium, nickel or graphite can be used as the carrier for the catalyst electrode 2 in the electrolyte space 5, the said carrier being activated on the surface with platinum metals, e.g. iridium, rhodium, ruthenium, platinum, palladium, oxides of these, silver, gold, cobalt aluminum spinel, doped lanthanum cobaltide, oxygen-tranferring cobalt, manganese and iron phthalocyanines, iron-dibenzo-tetra-aza-annulenes, cobalt(II)-bis(salicylidene-ethylene-diamines) or cobalt-tetra-aza-annulenes. These activators can be used individually or as a combination of several activators.

Catalyst electrodes 2 which are preferably used in the electrolyte space 5 are those which consist of graphite or graphite-coated carriers which have been subjected to partial anodic oxidation in aqueous nitric acid and then doped with molybdenum and/or tungsten(VI) oxides and alkali metal sulfides or molybdenum(VI) oxides and iodates. These electrode materials may furthermore contain electron-conducting and ion-conducting substances. Instead of molybdenum and/or tungsten(VI) oxides, it is also possible to use partially reduced vanadium(V) oxy compounds, such as vanadium(V) oxide, vanadium(IV) oxide, tellurium(VI) compounds, such as telluric acid or tellurium trioxide, and selenium(VI) compounds, e.g. selenic acid or selenium trioxide.

Other suitable electrodes 2 in the electrolyte space 5 are those consisting of titanium, and possessing coatings of metallic iridium, platinum, rhodium, palladium, gold or silver, or oxides of these, in combination with titanium suboxide or titanium carbide, and coatings of 4-tert.-alkyl-iron or manganese phthalocyanines or sulfonated products of these, which are applied in combination with ion exchanger and electron-conducting substances or with binders containing such substances.

To improve the electron exchange conditions at the polarized electrode 1 and to save enzymes, enzymes and microorganisms are immobilized at this superficially oxidized electrode 1 by means of adsorption. Adsorptive immobilization is preferably effected in enzyme-containing and/or microorganism-containing electrolyte buffers, e.g. phosphate buffer solutions. Other suitable carriers for the enzymes and microorganisms on the polarized electrode 1 are, for example, nickel/nickel oxide, titanium suboxide, zeolites, sepharose, cyanuric chloride/graphite, carbodiimide/graphite, porous copolymers of styrene and divinylbenzene and macroporous organic cation exchangers and anion exchangers, for example polymers and copolymers of styrene and divinylbenzene, vinyl chloride and acrylonitrile, olefins, and perfluorinated olefins, which possess, as charge-carrying groups, quaternary ammonium, sulfo or carboxyl groups. It is advantageous if the enzyme-carrying compounds are fixed on the electrode surface with ion-conducting and electron-conducting organic or inorganic substances.

Where auxiliary cathodes are employed, for example, iron, nickel, cobalt, graphite or chrome nickel steels are used as electrode materials.

Figure 1:
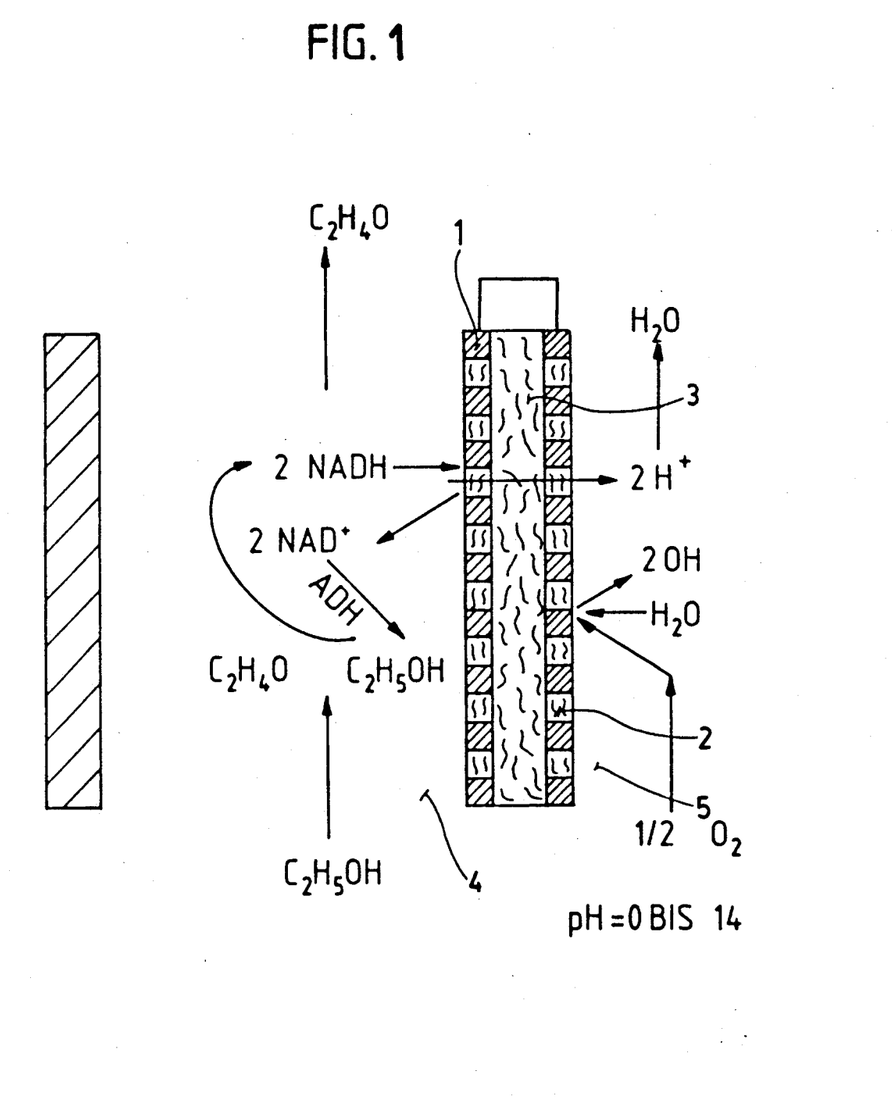
FIG. 1 shows the polarization of an electrode 1 by a catalyst electrode 2 at which the oxidizing agents are reduced, the two electrodes 1 and 2 being connected via a low resistance.
Figure 2:
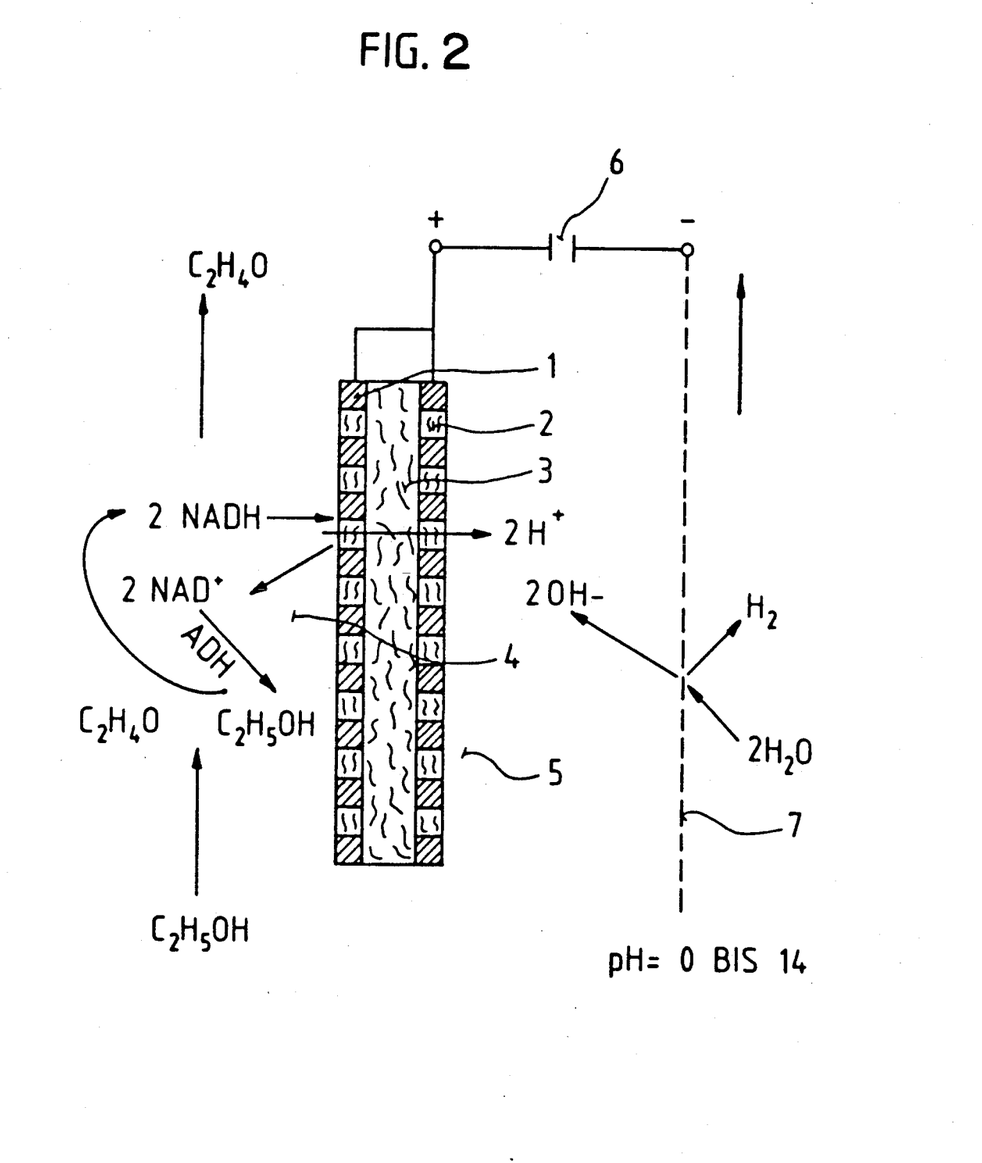
FIG. 2 shows the polarization of the electrode 1, which is connected to the catalyst electrode 2 via a low resistance, by means of an external voltage source 6 against an auxiliary cathode 7.
Figure 3:
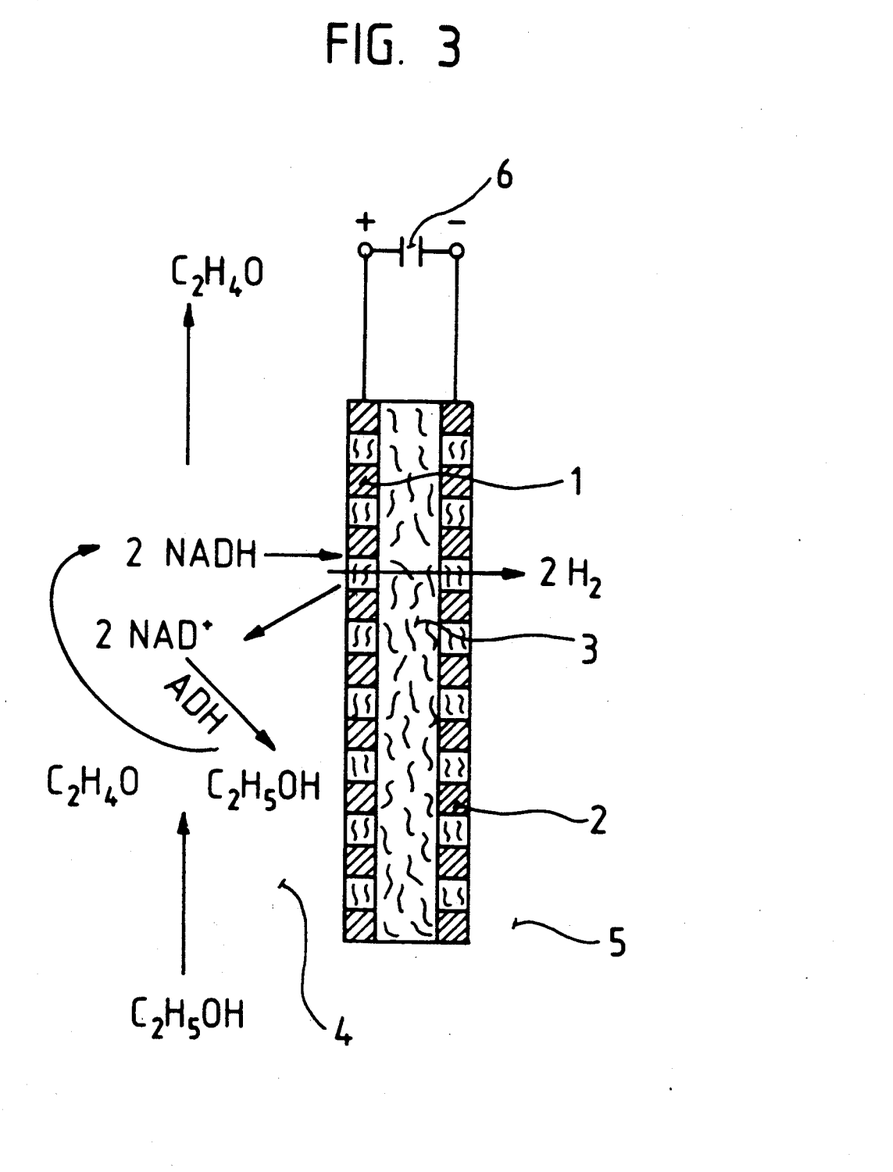
FIG. 3 shows the polarization of the electrode 1 against the catalyst electrode 2 by means of an external voltage source 6.

FIG. 1 shows a fuel cell for enzyme regeneration which possesses an oxygen reduction electrode as the catalyst electrode 2, the polarized electrode 1 being connected via a low resistance to the catalyst electrode 2. The reactor space 4 (anode space) and the electrolyte space 5 (cathode space) are separated by a polyelectrolyte 3. Both electrodes are fixed to the polyelectrolyte surface 3 (ion exchanger). When the cell is operated, the reduced enzyme (NAD) is regenerated, and equivalent amounts of oxygen are reduced at the catalyst electrode 2.

Figure 4:
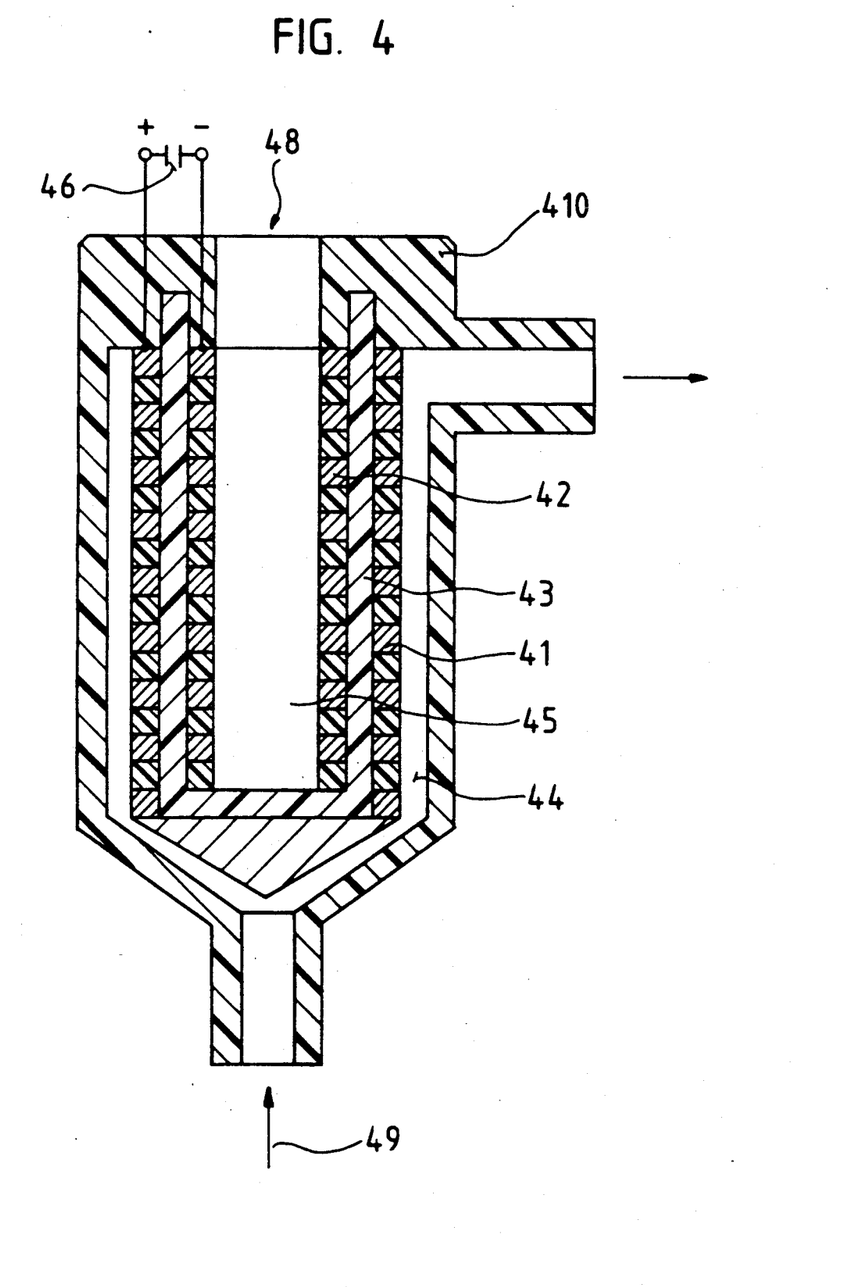
FIGS. 4 to 6 show various embodiments of tubular reactors.

FIG. 4 shows a tubular reactor in which the electrode 41 and the catalyst electrode 42 each consist of expanded metal and are fixed to the polyelectrolyte 43. The electrode 41 is polarized against the catalyst electrode 42 via an external voltage source 46. The reactor wall 410 consists of polypropylene. The electrolyte space 45 containing the electrolyte 48 is separated from the reactor space 44 containing the reaction medium 49 by means of the polyelectrolyte 43.

Figure 5:
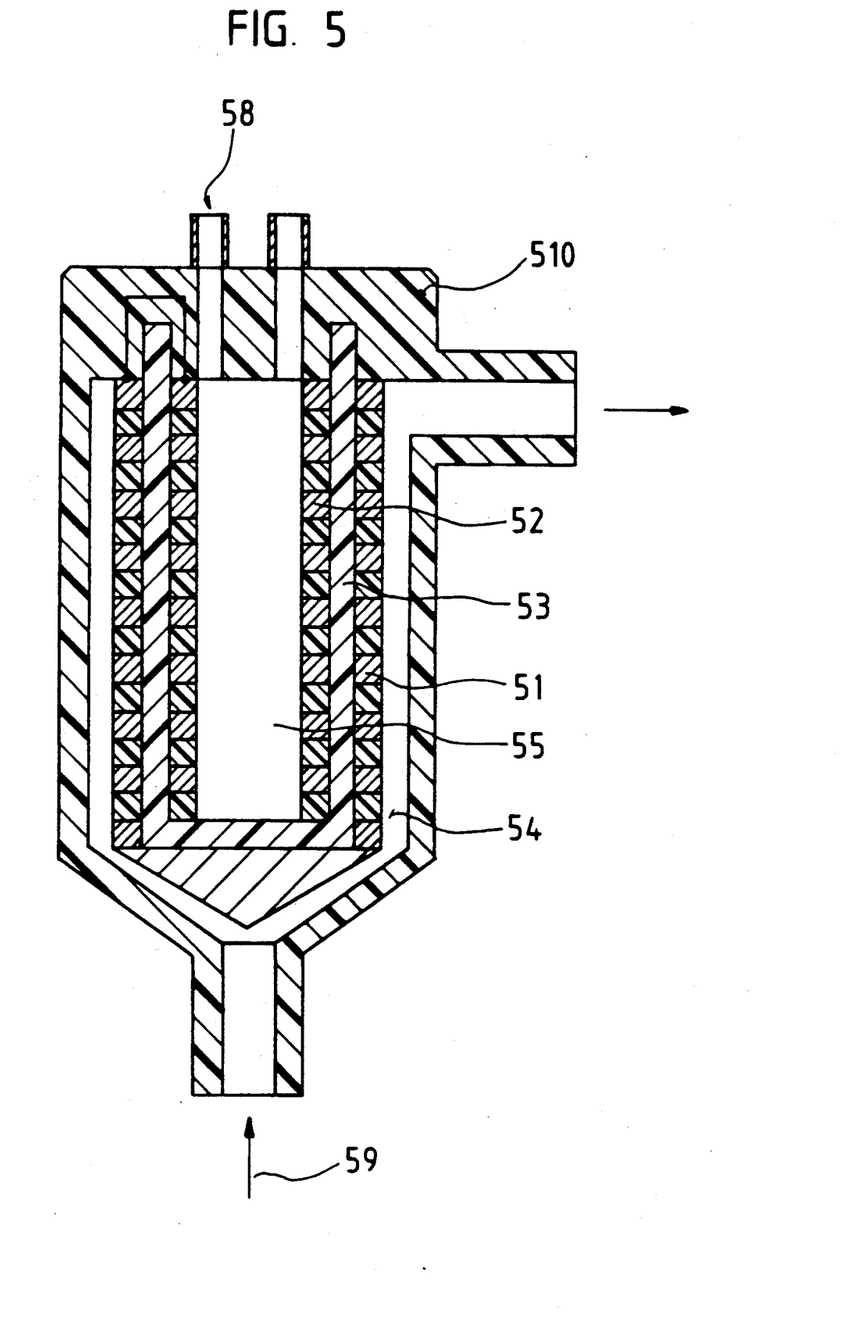

FIG. 5 shows a tubular reactor in which the electrode 51 is connected via a low resistance to the catalyst electrode 52. Both electrodes 51 and 52 consist of expanded metal and are fixed to the polyelectrolyte 53. The electrolyte space 55, which is operated with the oxidizing agent 58, is separated from the reactor space 54 containing the reaction medium 59 by means of the polyelectrolyte 53. The reactor wall 510 likewise consists of polypropylene.

Figure 6:
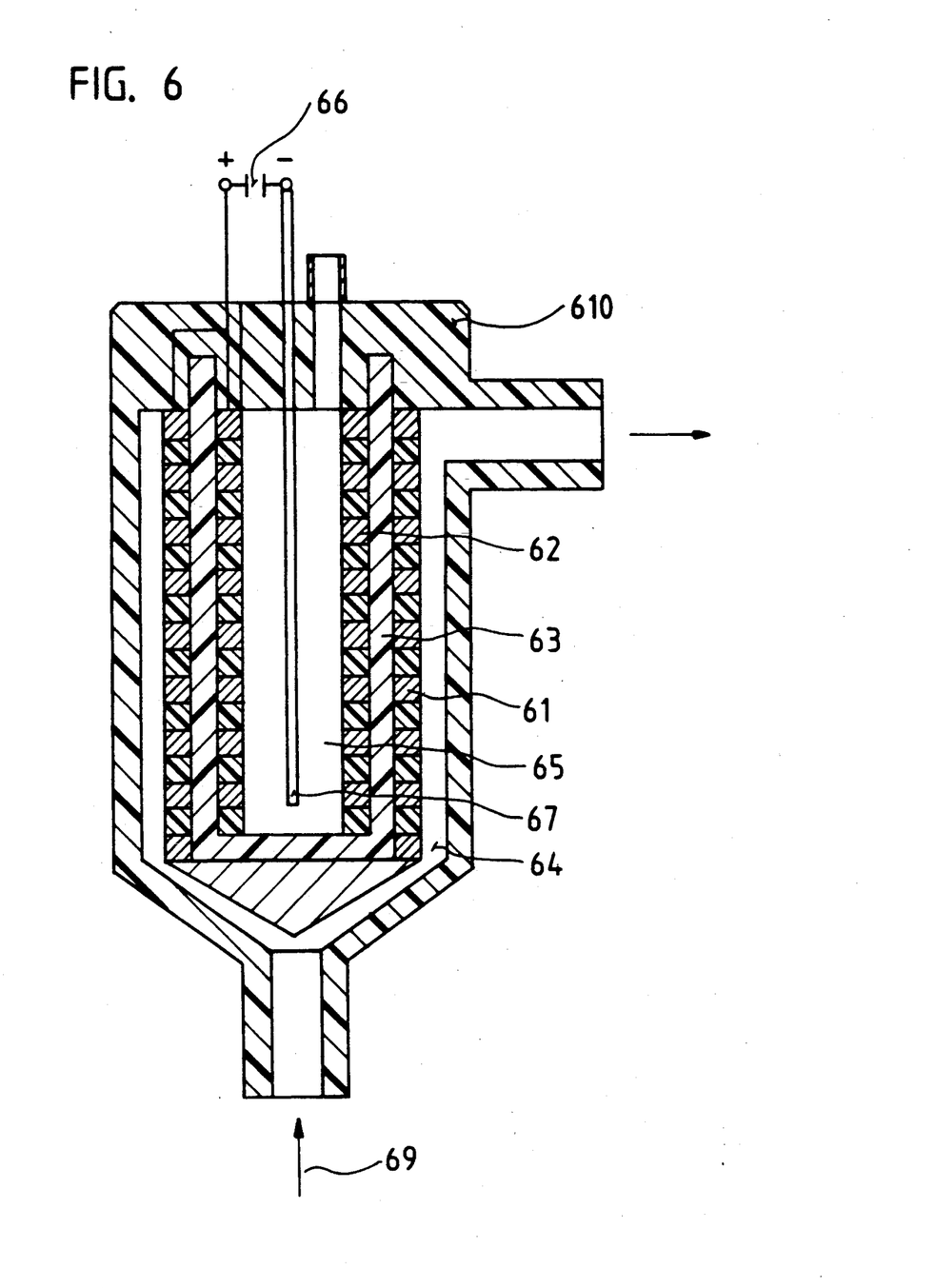

FIG. 6 shows a tubular reactor in which the electrode 61 is connected via a low resistance to the catalyst electrode 62. The latter is polarized against an auxiliary electrode 67 by means of an external voltage source 66.

The electrolyte space 65 is separated from the reactor space 64 containing the reaction medium 69 by means of the polyelectrolyte 63. The reactor wall 610 consists of polyethylene.

EXAMPLE 1

A tubular reactor having the structure shown in FIG. 5 contains a polyelectrolyte 53 which is prepared by copolymerization of tetrafluoroethylene with unsaturated perfluorinated ethers containing terminal sulfonyl fluoride groups and serves to separate the reactor space 54 from the electrolyte space 55 and is a carrier for the polarized electrode 51. The polyelectrolyte 53 has a diameter of 30 mm, a length of 220 mm and a wall thickness of 0.85 mm. Expanded titanium metal having a mesh size of 6×13 mm, a web width of 2.5 mm, an active surface area of 1.98 m$^2$/m$^2$ of geometrical surface and a free cross-section of 36% is fixed to the polyelectrolyte side located in the reactor space 54, the said expanded titanium metal being coated on the surface with graphite. The surface of the graphite is activated by anodic oxidation at 2 kA/m$^2$ in 50% strength by weight aqueous nitric acid, followed by cathodic reduction in 10% strength sulfuric acid. Expanded titanium metal having a mesh size of 7×12.5 mm, a web width of 2 mm, an active surface area of 1.82 m$^2$/m$^2$ of geometrical surface area and a free cross-section of 33% is located on the polyelectrolyte surface 53 in the electrolyte space 55. This expanded metal is coated with graphite which has been subjected to partial anodic oxidation in 50% strength aqueous nitric acid, and is doped with hydrated Mo(VI) oxide and K$_2$S. The two electrodes (expanded metals) are connected via a low-resistance titanium bow. The distance between the anodically polarized electrode surface in the reactor space and the reactor wall is 3 mm in order to ensure good conversion. The electrolyte space 55 is filled with 5% strength aqueous sulfuric acid to which 0.4% by weight of iron(III) nitrate is added. Oxygen is introduced, as the oxidizing agent 58, into the electrolyte space 55. The reaction medium, e.g. beet syrup, flows through the reactor space at a rate of from 0.3 to 2.5 m/sec, the enzymes being regenerated at the polarized electrode 51 or the microorganisms being respirated. The reactor can be employed for the preparation of glutamic acid from starch, cane syrup or beet syrup if mutants of Corynebacterium glutamicum are used as microorganisms.

EXAMPLE 2

A tubular reactor having the structure shown in FIG. 5 contains a polyelectrolyte 53 which is prepared by copolymerization of tetrafluoroethylene with unsaturated perfluorinated ethers containing terminal sulfonyl fluoride groups and carboxylic acid ester groups, and serves to separate the reactor space 54 from the electrolyte space 55 and as a carrier for the electrodes 51 and 52. Platinized expanded titanium metal having a mesh size of 6×13 mm, a web width of 2.5 mm, an active surface area of 1.98 m$^2$/m$^2$ of geometrical surface area and a free cross-section of 36% is fixed to the polyelectrolyte side located in the reactor space 54. The surface of the expanded metal is covered with from 0.5 to 0.8 mm thick graphite wool obtained by heating cotton wool at +2,500° C. in an inert gas atmosphere. The graphite wool is oxidized in 50% strength by weight aqueous nitric acid at an anodic current density of 2 kA/m$^2$ and at +26° C. The oxidation potential $\epsilon_h$ is ~+2.12 V. Residual nitric acid is removed after the oxidation by cathodic reduction in 10% strength aqueous sulfuric acid. In the electrolyte space 55, platinized expanded titanium metal with graphite wool is applied on the polyelectrolyte surface 53, as in the reactor space. The graphite wool is impregnated with hydrated vanadium pentoxide which additionally contains titanium(IV) oxide and titanium vanadate. The two electrodes 51 and 52 are connected via a low-resistance titanium bow. The electrolyte space 55 is filled with 5% strength by weight sulfuric acid containing 1% by weight of iron(III) sulfate and is gassed with oxygen. The electrode 51 in the reactor space 54 is impregnated with a phosphate buffer at pH 7 which contains 1 mole of alcohol dehydrogenase (ADH) from Leuconostoc, so that ADH is immobilized on the surface of the graphite wool. During operation of the reactor, alcohols are converted to aldehydes at the polarized electrode 51 in the reactor space 54 without the coenzyme nicotinamide adenine dinucleotide (NAD) being required.

However, the electrode 51 may also be additionally impregnated with coenzymes.

Instead of atmospheric oxygen, it is also possible to use hydrogen peroxide as the oxidizing agent in the electrolyte space 55. In this case, the addition of iron-(III) ions is dispensed with.

We claim:

1. A biological reactor for the oxidative conversion of organic compounds comprising:
    means defining a reactor chamber and an electrolyte chamber, said means including an ion exchange membrane which separates the reactor chamber from the electrolyte chamber;
    an anodically polarized electrode made of an electrically conductive carbon material which has been subjected to a surface oxidation at a potential of $\epsilon_h$ of from +1.3 to +10.0 V in an aqueous oxygen-containing mineral acid and then activated by cathodic reduction in aqueous mineral acid and to which at least one biocatalyst selected from the group consisting of enzymes and microorganisms is adsorptively immobilized, said anodically polarized electrode being present in the reactor chamber and separated from the electrolyte chamber by the ion exchange membrane;
    a polarizable catalyst electrode which is permeable to ions and electrically conductive, said catalyst electrode being present in the electrolyte chamber and separated from the reactor chamber by the ion exchange membrane.

2. The reactor of claim 1 wherein the anodically polarized electrode is fixed to the ion exchange membrane and the polarizable catalyst electrode is fixed to the ion exchange membrane.

3. The reactor of claim 1 wherein the polarizable catalyst electrode is connected to the anodically polarized electrode via an external voltage source.

4. The reactor of claim 1 wherein the polarizable catalyst electrode and anodically polarized electrode are connected to an external voltage source and an auxiliary cathode.

5. The reactor of claim 1 wherein coenzymes are also immobilized on said anodically polarized electrode.

6. The reactor of claim 1 wherein the anodically polarized electrode consists of graphite, graphite wool or active carbon which has been subjected to partial electrochemical oxidation in aqueous nitric acid and then activated by cathodic reduction in mineral acid.

7. The reactor of claim 1 wherein the ion exchange membrane consists of heterogeneous or homogeneous cation exchange or anion exchange membranes.

8. The reactor of claim 1 wherein the polarizable catalyst electrode and anodically polarized electrode are in the form of felts, rods, expanded metals, sintered elements perforated plates, nets, expanded metal lattices, grids or sponges.

9. The reactor of claim 1 wherein the polarizable catalyst electrode and anodically polarized electrode contain holes, pores, channels or perforations.

10. The reactor of claim 9 wherein said holes, pores channels or perforations are partially or completely filled with said ion exchange membrane.

11. The reactor of claim 1 wherein the catalyst electrode consists of graphite which is partially oxidized on the surface and is doped with at least one of molybdenum and tungsten(VI) and alkali metal sulfides or molybdenum(VI) oxides and iodates.

12. The reactor of claim 1 wherein the catalyst electrode is doped on the surface with oxygen-carrying metal chelates and a binder which is ion-conducting and electron-conducting or contains ion-conducting and electron-conducting substances.

13. The reactor of claim 1 wherein the catalyst electrode consists of graphite which is partially oxidized on the surface and doped with vanadium IV, vanadium V, iron(III), titanium(III), titanium(IV) or combinations thereof.

* * * * *